United States Patent
Bae et al.

(10) Patent No.: US 10,543,254 B2
(45) Date of Patent: Jan. 28, 2020

(54) COMPOSITION CONTAINING NEUROPEPTIDE Y FOR INHIBITING SIDE EFFECTS OF ANTICANCER AGENTS

(71) Applicant: KYUNGPOOK NATIONAL UNIVERSITY INDUSTRY-ACADEMIC COOPERATION FOUNDATION, Daegu (KR)

(72) Inventors: Jae Sung Bae, Daegu (KR); Hee Kyung Jin, Daegu (KR); Min Hee Park, Gyeongsangbuk-do (KR)

(73) Assignee: KYUNGPOOK NATIONAL UNIVERSITY INDUSTRY—ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/323,402

(22) PCT Filed: Jul. 14, 2015

(86) PCT No.: PCT/KR2015/007309
§ 371 (c)(1),
(2) Date: Dec. 30, 2016

(87) PCT Pub. No.: WO2016/010346
PCT Pub. Date: Jan. 21, 2016

(65) Prior Publication Data
US 2017/0189491 A1    Jul. 6, 2017

(30) Foreign Application Priority Data

Jul. 14, 2014  (KR) .................. 10-2014-0088589

(51) Int. Cl.
*A61K 38/22* (2006.01)
*A61K 38/17* (2006.01)

(52) U.S. Cl.
CPC ............................. *A61K 38/2271* (2013.01)

(58) Field of Classification Search
None
See application file for complete search history.

(56) References Cited

U.S. PATENT DOCUMENTS

2006/0263368 A1* 11/2006 Rosenblum ........ A61K 41/0038
424/155.1

OTHER PUBLICATIONS

Langer et al., J. Med. Chem., 2001, vol. 44:1341-1348.*
Korner et al., Lab. Invest., 2004, vol. 84(1):71-80.*
Helm et al., J. Ovarian Res., 2009, vol. 2:2.*
Park et al., Neuropeptide Y regulates the hematopoietic stem cell niche in bone marrow, N-15, Poster Session, May 14-16, 2014 (2014), Korean Society for Biochemistry and Molecular Biology (KSBMB) Annual Meeting, COEX, Seoul, Korea.
Broqua et al., Antinociceptive effects of neuropeptide Y and related peptides in mice, Brain Res., 724:25-32 (1996).
Clarke et al., Coronary artery infusion of neuropeptide Y in patients with angina pectoris, Lancet, May 9;1(8541):1057-9 (1987).
International Search Report (Translation), International Application No. PCT/KR2015/007309, dated Oct. 26, 2015).
Intondi et al., Intrathecal neuropeptide Y reduces behavioral and molecular markers of inflammatory or neuropathic pain, Pain, 137:352-65 (2008).
Portenoy et al., Management of cancer pain, Lancet, 353:1695-700 (1999).
Quasthoff et al., Chemotherapy-induced peripheral neuropathy, J. Neurol., 249:9-17 (2002).

* cited by examiner

*Primary Examiner* — Xiaozhen Xie
(74) *Attorney, Agent, or Firm* — Cantor Colburn LLP

(57) ABSTRACT

Provided is a composition containing neuropeptide Y for inhibiting side effects of anticancer agents. The neuropeptide Y of the present invention exhibits an effect of mitigating side effects, especially bone marrow injury and neurological disorders, occurring due to the administration of anticancer agents, and thus may be useful as an anticancer adjuvant which may mitigate side effects of anticancer agents and enhance the effect of anticancer agents.

5 Claims, 9 Drawing Sheets

COMPOSITION CONTAINING NEUROPEPTIDE Y FOR INHIBITING SIDE EFFECTS OF ANTICANCER AGENTS

TECHNICAL FIELD

The present invention relates to a composition containing neuropeptide Y for inhibiting side effects of anticancer agents.

Further, the present invention relates to an anticancer adjuvant containing neuropeptide Y as an active ingredient.

Further, the present invention relates to a pharmaceutical composition containing neuropeptide Y as an active ingredient for preventing or treating bone marrow injury.

Further, the present invention relates to a pharmaceutical composition containing neuropeptide Y as an active ingredient for preventing or treating neurological disorders.

Further, the present invention relates to a food composition containing neuropeptide Y as an active ingredient for mitigating side effects of anticancer agents.

BACKGROUND ART

Recently, causes of deaths from cancer of all causes of deaths have been continuously increased by one in four persons. As such, therapeutic methods of cancer occupying most of causes of deaths include surgery, radiotherapy, biotherapy, chemotherapy, and the like.

Among them, an anticancer agent used in the chemotherapy is introduced to the metabolic pathway of cancer cells and directly acts with DNA to interrupt replication, transcription, and translation of DNA or interfere with the synthesis of nucleic acid precursors and inhibit cell division and thus has cytotoxicity to the cells. Accordingly, since at the time of administration, the anticancer agent causes serious injury to normal cells and causes bone marrow hematopoiesis, immunosuppression, hair loss, diarrhea, gastrointestinal disorders, liver and kidney toxicity, and the like, researches for minimizing side effects of the anticancer agent and increasing therapeutic effects are urgently required.

The anticancer agents developed until now have a characteristic in which therapeutic and toxic effects are mostly overlapped because of no cancer-specific selectivity, and the occurrence of toxicity has relevance to whether the drug may be concentrated in the plasma. The toxicity due to administration of the anticancer agents has various side effects including hematocytopenia of white blood cells, platelets and red blood cells due to bone marrow injury, hair loss symptoms due to hair follicle cell destruction, menstrual irregularity due to side effects on ovaries, male infertility due to side effects on testicles, stomatitis due to side effects caused by mucosal cell destruction of the digestive tract, nausea-vomiting, swallowing disorders and digestive disorders, diarrhea symptoms, renal toxicity due to tubulorrhexis, peripheral neuritis and weakness caused by nervous system disorders, vascular disorders such as vascular pain and rash, skin and nail discoloration, and the like.

As the most common side effect caused by administration of the anticancer agents, nausea and vomiting are included. The degree of causing nausea and vomiting is various according to the anticancer agents, and nausea and vomiting caused by administrating cisplatin which is frequently used in kidney cancer and lung cancer are very serious, and in loss of appetite, the vomiting is easily caused and particularly, cisplatin has toxicity in kidneys and liver. Various antivomiting drugs are selected and combined according to clinical symptoms to be used before and after anticancer therapy and vomiting may be successfully adjusted by administration of various routes and times, but the quality of life is greatly deteriorated.

Ondansetron used for suppressing acute and delayed vomiting causes allergic reaction, irregular heartbeat, muscle cramps, and secondary side effects of being unable to move, metoclopramide has side effects including nervousness, dyspnea, insomnia, heart attack, and the like, and diazepam has side effects including bronchial pain, rash, hallucinations, and the like.

Further, for the purpose of mitigation of side effects of anticancer agents, increased efficacy of chemotherapy, increased survival rate of cancer patients, improved quality of life, and the like, various anticancer adjuvants are used, but also cause secondary side effects. Interferon, interleukin, and the like having excellent antitumor and immune enhancement are protein formulations and have a disadvantage that the price is expensive. Mesna™ used for preventing urine toxicity has side effects including nausea, vomiting, decreased appetite, gastrointestinal pain, diarrhea, fever, dizziness, and the like, and Aminfostine™ for free-radical cleaning cannot be continuously administrated before 24 hrs after being administrated because of antihypertensive action.

DISCLOSURE

Technical Problem

The inventors exerted all possible efforts to develop a drug capable of mitigating side effects of anticancer agents as described above and thus verified that neuropeptide Y effectively improves side effects of anticancer agents, and completed the present invention.

The present invention is directed to provide a composition for inhibiting side effects of anticancer agents.

The present invention is also directed to provide an anticancer adjuvant.

The present invention is also directed to provide a pharmaceutical composition for preventing or treating bone marrow injury.

The present invention is also directed to provide a pharmaceutical composition for preventing or treating neurological disorders.

The present invention is directed to provide a food composition for mitigating side effects of anticancer agents.

Technical Solution

One aspect of the present invention provides a pharmaceutical composition containing neuropeptide Y as an active ingredient for inhibiting side effects of anticancer agents.

The side effect of anticancer agents may be selected from a group consisting of bone marrow injury, hematocytopenia due to bone marrow destruction, hair loss, menstrual irregularities, male infertility, stomatitis, vomit, dysphagia, digestive disorders, diarrhea, toxic nephropathy, neurological disorders, vascular disorders, skin or nail discoloration, dyspnea, hearing loss, tinnitus, peripheral neuritis, convulsions, hypersensitivity reaction, cardiovascular reaction, neurokinetic toxicity, neurosensory toxicity, myalgia, arthralgia, nausea, fever, anemia, anorexia, helplessness, nausea, constipation, fatigue, infection, hematuria, proteinuria, allergy, abdominal cramps, cell necrosis, and tissue necrosis. Preferably, the side effect of anticancer agents may be bone marrow injury or neurological disorders.

Further, the anticancer agent may be selected from a group consisting of cisplatin, doxorubicin, etoposide, paclitaxel, doxetaxel, fluoropyrimidine, oxalplatin, camptothecan, belotecan, podophyllotoxin, vinblastine sulfate, cyclophosphamide, actinomycin, vincristine sulfate, methotrexate, bevacizumab, thalidomide, eriotinib, gefitinib, camptothecin, tamoxifen, anasterozole, gleevec, 5-fluorouracil (5-FU), floxuridine, leuprolide, flutamide, zoledronate, vincristine, gemcitabine, streptozocin, carboplatin, topotecan, irinotecan, vinorelbine, hydroxyurea, valrubicin, retinoic acid, meclorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenyltazone, cyclophosphamide, mechlorethamine, dexamethasone, prednisolone, celecoxib, valdecoxib, nimesulide, cortisone, and corticosteroid. Preferably, the anticancer agent may be cisplatin.

Further, the anticancer agent may be an anticancer agent for cancer selected from a group consisting of adrenocorticotropic hormone (ACTH) produced tumors, acute lymphocytic or lymphoblastic leukemia, acute or chronic lymphocytic leukemia, acute non-lymphocytic leukemia, bladder cancer, brain tumors, breast cancer, chronic myelogenous leukemia, colon cancer, T-zone lymphoma, endometriosis, esophagus cancer, bile bladder cancer, Ewing's sarcoma, head and neck cancer, tongue cancer, Hopkins lymphoma, Kaposi's sarcoma, kidney cancer, liver cancer, lung cancer, mesothelioma, multiple myeloma, neuroblastoma, non-hopkin lymphoma, osteosarcomas, ovarian cancer, neuroblastoma, lobular carcinoma, cervical cancer, prostate cancer, pancreatic cancer, colon cancer, penis cancer, retinoblastoma, skin cancer, stomach cancer, thyroid cancer, uterine cancer, testicular cancer, Wilms tumor, and tropoblastoma.

Another aspect of the present invention provides an anticancer adjuvant containing neuropeptide Y as an active ingredient.

Yet another aspect of the present invention provides a pharmaceutical composition containing neuropeptide Y as an active ingredient for preventing or treating bone marrow injury.

Still another aspect of the present invention provides a pharmaceutical composition containing neuropeptide Y as an active ingredient for preventing or treating neurological disorders.

Still yet another aspect of the present invention provides a food composition containing neuropeptide Y as an active ingredient for mitigating side effects of anticancer agents.

Still yet another aspect of the present invention provides a method for inhibiting side effects of anticancer agents including administrating a pharmaceutically acceptable amount of neuropeptide Y to a subject.

Still yet another aspect of the present invention provides a method for treating or preventing bone marrow injury or neurological disorders of a subject including administrating a pharmaceutically acceptable amount of neuropeptide Y to a subject.

Advantageous Effects

The neuropeptide Y of the present invention exhibits an effect of mitigating side effects, especially bone marrow injury and neurological disorders, occurring due to the administration of anticancer agents, and thus may be useful as an anticancer adjuvant which may mitigate side effects of anticancer agents and enhance the effect of anticancer agents.

Figure 1:
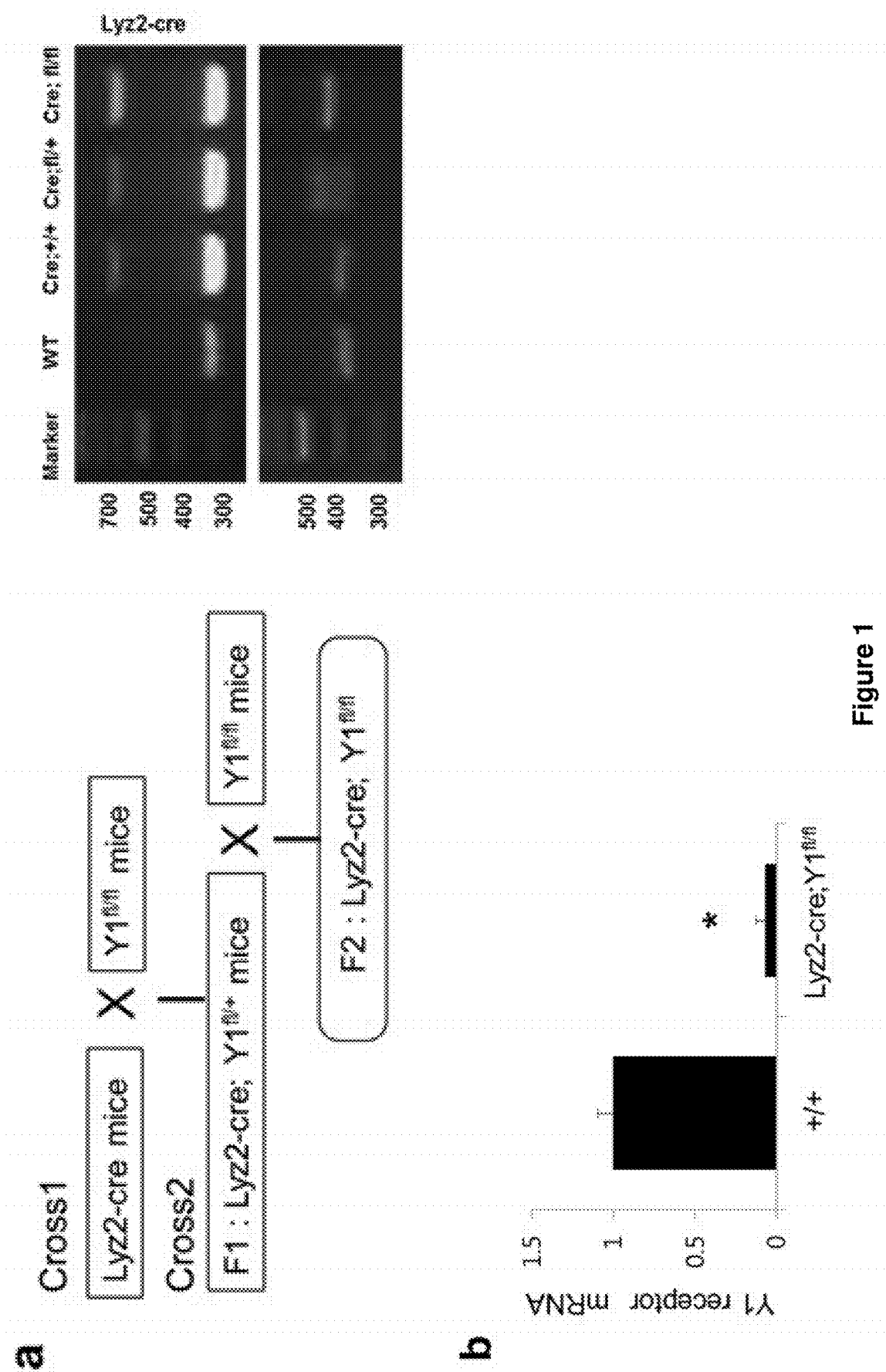
FIG. 1A illustrates a mating schematic diagram for reducing a Y1 receptor in macrophages by using Lyz2-cre and $Y1^{fl/fl}$ mice (left side) and PCR-based genotyping for verifying Lyz2-cre; $Y1^{fl/fl}$ mice (right side).
FIG. 1B illustrates expression of a Y1 receptor in macrophages cultured from BM of control, Lyz2-cre; $Y1^{fl/fl}$ mice (n=5 mice per group).
FIG. 1C illustrates a mating schematic diagram for reducing a Y1 receptor in osteoblasts by using Col1a1-cre and $Y1^{fl/fl}$ mice (left side) and PCR-based genotyping for verifying Col1a1-cre; $Y1^{fl/fl}$ mice (right side).
FIG. 1D illustrates that the osteoblasts are defined as $CD31^-Sca1^-CD51^+$ by using $CD45^-Lin^-$ gate. A classified group was verified through real-time PCR for osteoblasts-specific osteocalcin. In the osteoblasts classified from BM of each group, the Y1 receptor was measured. * p<0.05. Data was illustrated as mean±s.e.m.
Figure 1:
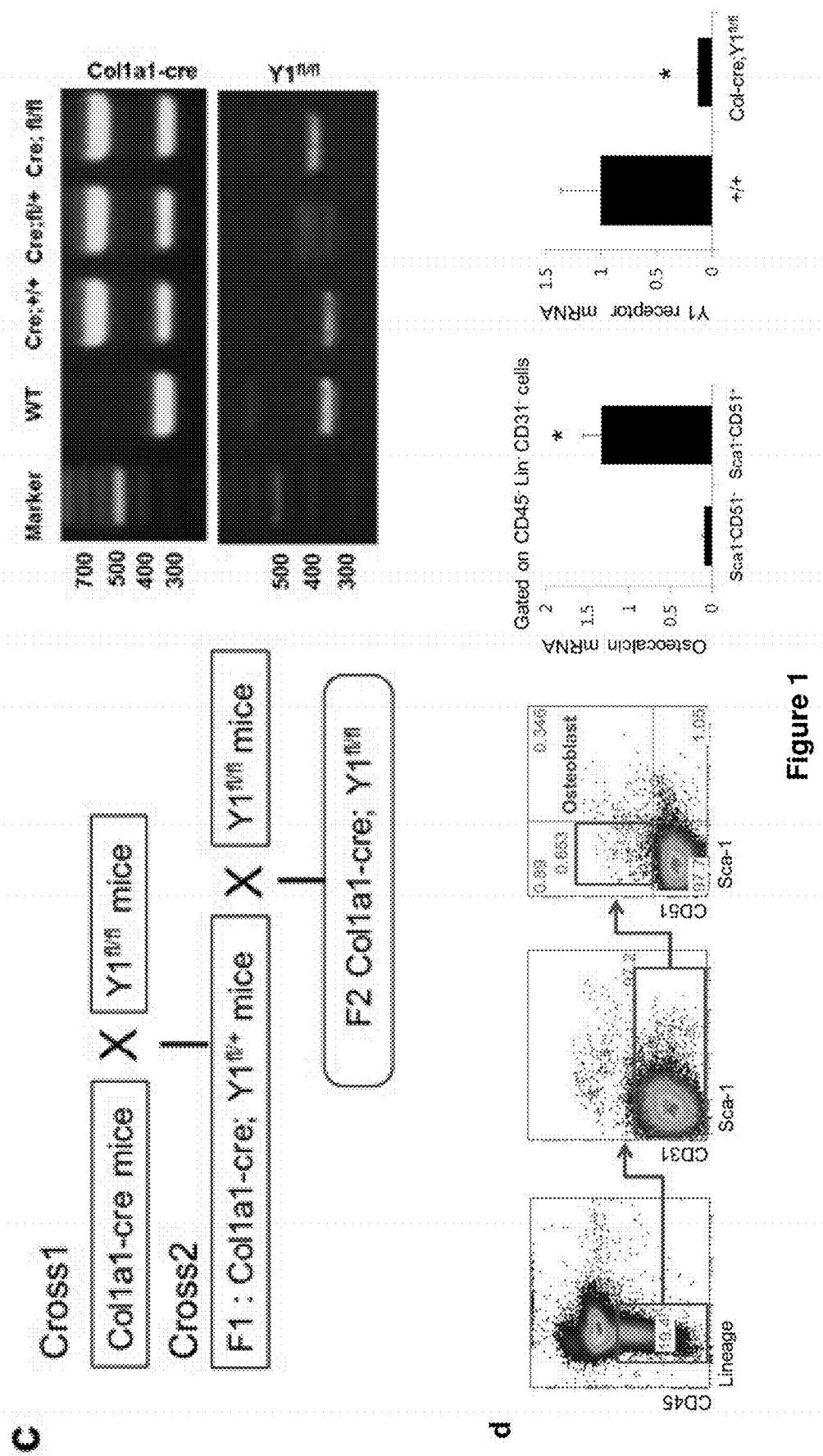

* p<0.05. An error bar illustrates mean±s.e.m.

MODES OF THE INVENTION

An aspect of the present invention provides a composition containing neuropeptide Y for inhibiting side effects of anticancer agents.

The composition includes a pharmaceutical composition or a food composition.

Hereinafter, the present invention will be described in detail.

In the present invention, neuropeptide Y (NPY) is 36-amino acid peptide and belongs to a family of neuroendocrine peptides consisting of a pancreatic polypeptide (PP). The corresponding peptide abundantly exists in the central and peripheral nervous system, especially the hypothalamus and the cortex of mammals. It is known that the NPY potentially exhibits a wide physiological effect in therapeutics and has a possibility of inducing vasoconstriction and causing angina when the NPY is administered alone (Clarke, et al., Lancet 1(8541):1057 (1987)). Further, it is known that the NPY is a neurotransmitter that is distributed in the central or peripheral nervous system and is increased in a starvation state to induce increased appetite and decreased energy metabolism. However, it is not reported that the neuropeptide Y may improve side effects of anticancer agents. Further, the neuropeptide Y of the present invention is a concept including a peptide consisting of some amino acids which exhibit the same or similar efficacy as all amino acids of the neuropeptide without limiting its origin.

In the present invention, the term "anticancer agent" is a generic term of chemotherapeutic agents used for treating malignant tumors, and most of anticancer agents mean drugs which are introduced to various metabolic pathways of cancer cells to mainly inhibit the synthesis of nucleic acids and exhibit anticancer activity. The anticancer agent has relatively low toxicity to normal cells and more selectively acts on cancer cells by using a difference in sensitivity to the drug between the normal cells and the cancer cells, but has side effects because normal cells also suffer some injury. The reason is that the anticancer agent does not act on only rapid-dividing cancer cells, but has an effect on bone marrow, gastrointestinal tract, hair root cells which are rapid-dividing normal cells, due to a property that acts anywhere in rapid-dividing cells. Accordingly, as common side effects of the drugs, temporary hematocytopenia, nausea, vomit, diarrhea, decreased appetite, hair loss, and the like are shown. The anticancer agents which have been currently used in cancer treatment are classified into six categories such as alkylating agents, metabolic antagonists, antibiotics, mitotic inhibitors, hormones and others according to a biochemical mechanism.

Examples of the side effects of the anticancer agents include bone marrow injury, hematocytopenia due to bone marrow destruction, hair loss, menstrual irregularities, male infertility, stomatitis, vomit, dysphagia, digestive disorders, diarrhea, toxic nephropathy, neurological disorders, vascular disorders, skin or nail discoloration, dyspnea, hearing loss, tinnitus, peripheral neuritis, convulsions, hypersensitivity reaction, cardiovascular reaction, neurokinetic toxicity, neurosensory toxicity, myalgia, arthralgia, nausea, fever, anemia, anorexia, helplessness, nausea, constipation, fatigue, infection, hematuria, proteinuria, allergy, abdominal cramps, cell necrosis, or tissue necrosis, but are not limited thereto. Particularly, most preferably, the side effects of anticancer agents of the present invention may be bone marrow injury or neurological disorders. The bone marrow injury may accompany symptoms such as hematocytopenia of leukocytes, thrombocytes, and erythrocytes due to bone marrow destruction.

Further, the neurological disorders include peripheral neuritis, neurokinetic toxicity, neuropsychiatric, neuropathy, or neuropathic pain, but are not limited thereto.

Examples of the anticancer agents include cisplatin, doxorubicin, etoposide, paclitaxel, doxetaxel, fluoropyrimidine, oxalplatin, campthotecan, belotecan, podophyllotoxin, vinblastine sulfate, cyclophosphamide, actinomycin, vincristine sulfate, methotrexate, bevacizumab, thalidomide, eriotinib, gefitinib, camptothecin, tamoxifen, anasterozole, gleevec, 5-fluorouracil (5-FU), floxuridine, leuprolide, flutamide, zoledronate, vincristine, gemcitabine, streptozocin, carboplatin, topotecan, irinotecan, vinorelbine, hydroxyurea, valrubicin, retinoic acid, meclorethamine, chlorambucil, busulfan, doxifluridine, vinblastin, mitomycin, prednisone, testosterone, mitoxantron, aspirin, salicylates, ibuprofen, naproxen, fenoprofen, indomethacin, phenyltazone, cyclophosphamide, mechlorethamine, dexamethasone, prednisolone, celecoxib, valdecoxib, nimesulide, cortisone, corticosteroid, or the like, and kinds thereof such as compounds, hormone agents, antibodies, or the like are not limited.

Further, the anticancer agents may be administrated for cancers, such as adrenocorticotropic hormone (ACTH) produced tumors, acute lymphocytic or lymphoblastic leukemia, acute or chronic lymphocytic leukemia, acute non-lymphocytic leukemia, bladder cancer, brain tumors, breast cancer, chronic myelogenous leukemia, colon cancer, T-zone lymphoma, endometriosis, esophagus cancer, bile bladder cancer, Ewing's sarcoma, head and neck cancer, tongue cancer, Hopkins lymphoma, Kaposi's sarcoma, kidney cancer, liver cancer, lung cancer, mesothelioma, multiple myeloma, neuroblastoma, non-hopkin lymphoma, osteosarcomas, ovarian cancer, neuroblastoma, lobular carcinoma, cervical cancer, prostate cancer, pancreatic cancer, colon cancer, penis cancer, retinoblastoma, skin cancer, stomach cancer, thyroid cancer, uterine cancer, testicular cancer, Wilms tumor, and tropoblastoma.

Most preferably, the composition of the present invention may inhibit bone marrow injury or neurological disorders due to cisplatin administration.

It is known that the cisplatin is a chemotherapeutic agent for treating kidney cancer and the drug inhibits cell division to have an anticancer effect. Tumor cells have a characteristic in which cell proliferation is not regulated but continuously occurs, and when the cisplatin which inhibit cell division of the tumor cells is treated, in some cancers, the cisplatin prevents proliferation of the tumor cells and thus an anticancer effect may be expected. In some cases, it is known that proliferation of tumor cells is inhibited and sizes of existing tumor cells may be decreased.

Further, the present invention may provide an anticancer adjuvant containing neuropeptide Y as an active ingredient.

In the present invention, the anticancer adjuvant means improving side effects exhibited when the anticancer agents are administered or enhancing the anticancer effect of existing anticancer agents.

The composition of the present invention may further include a carrier, an excipient, and a diluent which are pharmacologically or physiologically acceptable in addition to the neuropeptide.

The composition of the present invention may be formulated and used in various forms, such as oral formulations including powders, granules, tablets, capsules, suspensions, emulsions, syrups, aerosols, and the like, and sterile injectable solutions, for their own purposes and according to usual methods and may be administered orally or through various pathways including intravenous, intraperitoneal, subcutaneous, rectal, topical administration, and the like. A suitable example of the carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinylpyrrolidone, water, methyl hydroxybenzoate, propyl hydroxybenzoate, talc, magnesium stearate, mineral oil, and the like. The composition may further include a filler, an anti-coagulant, a lubricant, a wetting agent, a flavoring, an emulsifier, a preservative, and the like.

A solid formulation for oral administration includes a tablet, a pill, a powder, a granule, a capsule, or the like, and the solid formulation may be formulated by mixing at least one excipient, for example, starch, calcium carbonate, sucrose, lactose, gelatin, and the like with the composition. Further, lubricants such as magnesium stearate and talc may be used in addition to simple excipients.

A liquid formulation for oral administration corresponds to a suspension, a solution, an emulsion, a syrup, and the like, and may include various excipients, for example, a wetting agent, a sweetener, an aromatic agent, a preserving agent, and the like in addition to water and liquid paraffin as simple diluents which are commonly used.

A formulation for parenteral administration includes a sterile aqueous solution, a non-aqueous solution, a suspension, an emulsion, and a lyophilizing agent, and a suppository. As the non-aqueous solution and the suspension, propylene glycol, polyethylene glycol, vegetable oils such as olive oil, injectable ester such as ethyl oleate, and the like may be used. A base compound of the injection may include existing additives such as solubilizers, isotonic agents, suspending agents, emulsifiers, stabilizers and preservatives.

In the present invention, the "administration" means providing a specific material to a patient by any suitable method, and the administration pathway of the composition of the present invention may be orally or parenterally administrated through all general pathways which may reach a target tissue. Further, the composition may be administrated by any device in which the active material may move to a target cell.

In the present invention, the "patient" means animals such as human and monkey, dog, goat, pig, or rat with diseases of which symptoms may be improved by administrating the composition of the present invention. The composition according to the present invention may be applied to not only humans (treatment, inhibition or prevention) but also other commercially useful animals.

As another aspect, the present invention provides a pharmaceutical composition containing neuropeptide Y for preventing or treating bone marrow injury and neurological disorders. The composition of the present invention may be administrated in a combination of the disease therapeutic agent.

The composition the present invention is administrated with a pharmaceutically effective dose.

In the present invention, the "pharmaceutically effective dose" means a amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a pathway of administration, and an emission rate, duration of treatment, and simultaneously used drugs and other elements well-known in the medical field. The composition of the present invention may be administrated as an individual therapeutic agent or administrated in combination with other therapeutic agents, sequentially or simultaneously administrated with therapeutic agents in the related art, and administrated in single or multiple. It is important to administrate an amount capable of obtaining a maximum effect with a minimal amount without side effects by considering the elements and it may be easily determined by those skilled in the art.

Particularly, the effective dose of the compound according to the present invention may vary according to age, sex, and weight of the patient, and generally administrated by 1 mg to 50 mg, preferably 1 mg to 10 mg per kg body weight daily or every other day, or administrated one to three times per day.

However, since the effective dose may be decreased or increased depending on administration pathways, severity of diseases, sex, weight, age, and the like, the dose is not limited to the scope of the present invention in any way.

The neuropeptide Y of the present invention may be isolated from natural materials or synthesized by using methods which are well-known in the art.

The composition for mitigating the side effects of anti-cancer agents of the present invention includes all forms such as functional foods, nutritional supplements, health foods or food additives containing anticancer components having anticancer activity, and the composition for increasing the type of anticancer activity may be prepared in various forms according to general methods which are known in the art. For example, as the health foods, the neuropeptide Y of the present invention is prepared and drunken in forms of teas, juices, and drinks or ingested by granulation, encapsulation and powdering, but the preparing form is not limited to the examples.

The health foods of the present invention may include additional additives and are not particularly limited to the kinds thereof. Preferably, the addible functional foods may be prepared by adding the neuropeptide Y of the present invention to beverages (including alcoholic beverages), fruits and their processed food (e.g., canned fruits, bottled foods, jam, marmalade, etc.), fish, meat and their processed foods (e.g., ham, sausage, corn beef, etc.), breads and noodles (e.g., udon noodles, buckwheat noodles, ramen noodles, spaghetti, macaroni, etc.), juice, various drinks, cookies, sweet taffy, dairy products (e.g., butter, cheese, etc.), edible vegetable oils, margarine, vegetable proteins, retort foods, frozen foods, various seasonings (e.g., soybean paste, soy sauce, sauce, etc.), and the like.

Further, one aspect of the present invention may provide a method for inhibiting side effects of anticancer agents in subjects including administrating a pharmaceutically acceptable amount of neuropeptide Y to the subjects.

Further, one aspect of the present invention may provide a method for treating or preventing bone marrow injury or neurological disorders in subjects including administrating a pharmaceutically acceptable amount of neuropeptide Y to the subjects.

Hereinafter, the present invention will be described in more detail through Examples. However, these Examples are to exemplify the present invention and the scope of the present invention is not limited to these Examples.

Example 1: Experimental Animal and Treatment

Lyz2-cre (The Jackson Laboratory), 2.3-kB Col1a1-cre, and Y1 flox/flox mice were used in order to remove a Y1 receptor in osteoblasts and macrophages. The mice were disposed in an experimental group by using a block randomization method. In order to eliminate prejudice, data collection and data analysis were never involved. All mice experiments were approved by Kyungpook National University Institutional Animal Care and Use Committee.

Example 2: Drug Treatment

Cisplatin (Enzo; 10 mg per kg body weight once per week) was used to induce SNS injury. Mice received i.p.

injections of cisplatin for 7 weeks as described. The mice were euthanized after 2 weeks after the last injection of cisplatin (for full bone marrow recovery).

To assess neuroprotection from cisplatin, mice were injected i.p. with NPY (Bachem, H-6375) daily during the 7-week cisplatin treatment period.

Example 3: Bone Marrow Transplantation

The mice were lethally irradiated (10 Gy, two split doses) and injected with $1\times10^6$ BM from CD45.1$^+$ (BoyJ) mice. After 4 weeks, the mice were sacrificed, and bone marrow and blood were obtained for analysis.

Example 4: Flow Cytometry

BM was isolated from the tibiae and femurs of each mouse. Red blood cells (RBCs) were hemolyzed once for 5 min at 4° C. in 0.15 M $NH_4Cl$ (StemCell Technologies), washed once with PBS (Gibco), and counted using a hemocytometer. For detecting HSCs, MSCs, or osteoblasts, Lin$^+$ cells were removed by using magnetic depletion using biotinylated lineage-specific antibodies (CD5, CD45R, CD11b, Gr-1, and Ter-119), followed by depletion with MACs beads conjugated to a monoclonal anti-biotin (Miltenyi Biotec). For staining of HSCs, Lin$^-$ cells were stained with phycoerythrin PE-Cy7-conjugated antibodies to Sca1 (558162), APC-conjugated antibodies to c-Kit (553356), FITC-conjugated antibodies to CD48 (557484), and PE-conjugated antibodies to CD150 (561540), all from Sciences. For MSCs and osteoblasts staining, Lin$^-$ cells were stained with APC-Cy7-CD45 (557659), APC-CD31 (551262), PE-Cy7-Sca1 (558162), or PE-CD51 (551187) (all from BD Sciences). Cells were further stained with streptavidin-pacific blue (PB) (Invitrogen, S11222). Data were collected on a BD LSRII system and AriaIII (BD Sciences) and analyzed using FlowJo software (Tress Star).

Example 5: Quantification of Sensory Neuropathy Through Heated-Pad Assay

For measuring effects of different treatments on sensory responses, a hot-plate test was performed.

A hot plate (Leica) was maintained at 50° C. and each mouse was positioned on the end of the heated surface, first nociception, that is, a time until jumping or paw licking was measured. A cut-off time was set as 60 seconds. For the measurement, the heated surface was cleaned with a detergent and ethanol and a temperature was maintained at 50° C.

Example 6: Statistical Analysis

Comparisons between two groups were performed with Student⊙ t-test. In cases where more than two groups were compared to each other, a one-way analysis of variance (ANOVA) and Tukey⊙ HSD test were performed. Comparisons of overall survival were performed using a log-rank test. All statistical analyses were performed using SPSS statistical software. $P<0.05$ was considered to be significant.

Example 7: Verification of NPY/Y1 Receptor Pathway in Bone Marrow Injury

Chemotherapy causes acute bone marrow injury and impairs HSC function or bone marrow regeneration. In particular, chemotherapy drugs such as cisplatin and vincristine induce sympathetic neuropathy by reducing the expression of Th fibers. Based on these concepts, the inventors predicted that NPY might prevent or treat against chemotherapy-induced neuropathy or bone marrow dysfunction.

To prove this hypothesis, first, the Y1 receptor was reduced in peripheral macrophages and endosteal osteoblasts and Lyz2-cre recombined in the myeloid cell lineage was used. Further, it was determined whether niche cells exhibited a neuroprotective effect from SNS injury induced by the chemotherapy drugs using Col1a1-cre and Y1$^{fl/fl}$ breeding systems.

In FIGS. 1A to 1D, the results were illustrated.

FIG. 1A illustrates a mating schematic diagram for reducing a Y1 receptor in macrophages by using Lyz2-cre and Y1$^{fl/fl}$ mice (left side) and PCR-based genotyping for verifying Lyz2-cre; Y1$^{fl/fl}$ mice (right side).

FIG. 1B illustrates expression of a Y1 receptor in macrophages cultured from the BM of control, Lyz2-cre; Y1$^{fl/fl}$ mice (n=5 mice per group).

FIG. 1C illustrates a mating schematic diagram for reducing a Y1 receptor in osteoblasts by using Col1a1-cre and Y1$^{fl/fl}$ mice (left side) and PCR-based genotyping for verifying Col1a1-cre; Y1$^{fl/fl}$ mice (right side).

FIG. 1D illustrates that the osteoblasts are defined as CD31$^-$Sca1$^-$CD51$^+$ by using CD45$^-$Lin$^-$ gate. A classified group is verified through real-time PCR for osteoblasts-specific osteocalcin. In the osteoblasts classified from the BM of each group, the Y1 receptor was measured. * $p<0.05$. Data was illustrated as mean±s.e.m.

As illustrated in FIGS. 1A to 1D, Y1 receptor mRNA levels were markedly reduced in macrophages cultured from Lyz2-cre; Y1$^{fl/fl}$ mice and osteoblasts isolated from Col1a1-cre; Y1$^{fl/fl}$ mice, respectively.

Figure 2:
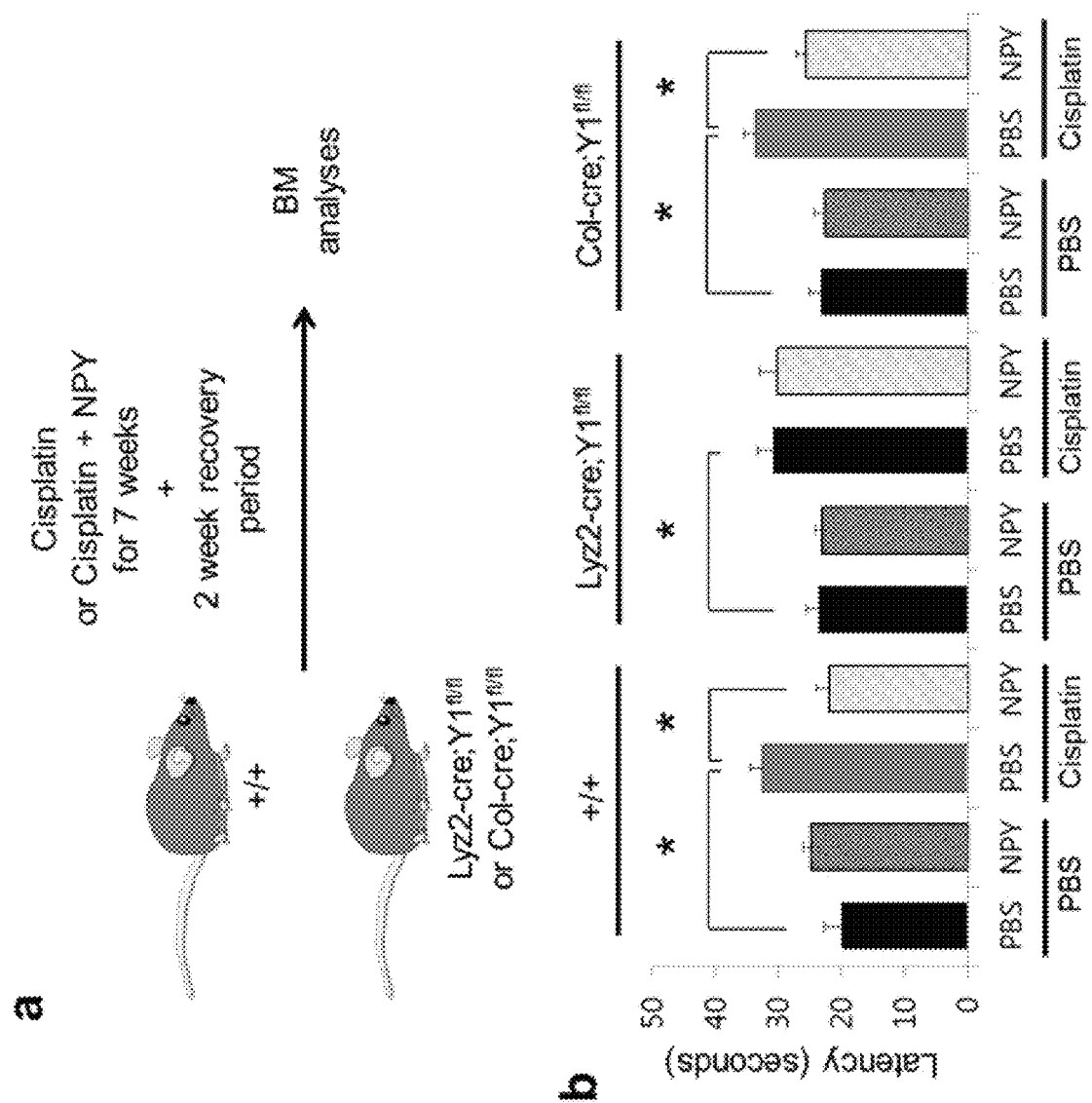
FIG. 2A is an experimental design for determining an effect of the Y1 receptor in the macrophages or osteoblasts in cisplatin-induced neuropathy, after NPY treatment.
FIG. 2B illustrates a quantitative analysis of sympathetic neuropathy (after 2 weeks after the last cisplatin injection) in control, Lyz2-cre; $Y1^{fl/fl}$ or Col1a1-cre; $Y1^{fl/fl}$ mice treated with cisplatin alone or cisplatin and NPY (n=6-10 mice per group, i.p). Latency illustrates a total time of a nociception signal of mice, that is, until jumping or paw licking.
FIG. 2C illustrates the number of BMNCs in control, Lyz2-cre; $Y1^{fl/fl}$ or Col1a1-cre; $Y1^{fl/fl}$ mice (n=4-6 mice per group) treated in FIG. 2A.
FIG. 2D illustrates a percentage of LSK cells and LT-HSCs in control, Lyz2-cre; $Y1^{fl/fl}$ or Col1a1-cre; $Y1^{fl/fl}$ mice (n=4-6 mice per group) treated in FIG. 2A.
FIG. 2E illustrates a quantitative analysis of $Th^+$ fibers in BM of each group (n=5-6 mice per group).
FIG. 2F illustrates the number of nestin-positive and $CD31^+$ endothelial cells per femoral region of each group (n=5-6 mice per group).
FIG. 2G illustrates a quantitative analysis of NPY expression in BM of each group (n=5-6 mice per group).
FIG. 2H illustrates an experimental design for verifying whether NPY protects $Th^+$ fibers from cisplatin-induced bone marrow injury and whether to accelerate posttransplant bone marrow recovery.
FIG. 2I illustrates a survival result of mice of each group (n=10-15 mice per group).
FIG. 2J illustrates the number of BMNCs (left side), a percentage of LSK cells (middle), and LT-HSCs (right side) in BM of WT mice treated with PBS, cisplatin or NPY, which are evaluated after 4 weeks after transplanting bone marrow. (n=5-6 mice per group).
FIG. 2K illustrates a percentage of nestin-positive and $CD31^+$ endothelial cells in the femur of each group.
Figure 2:
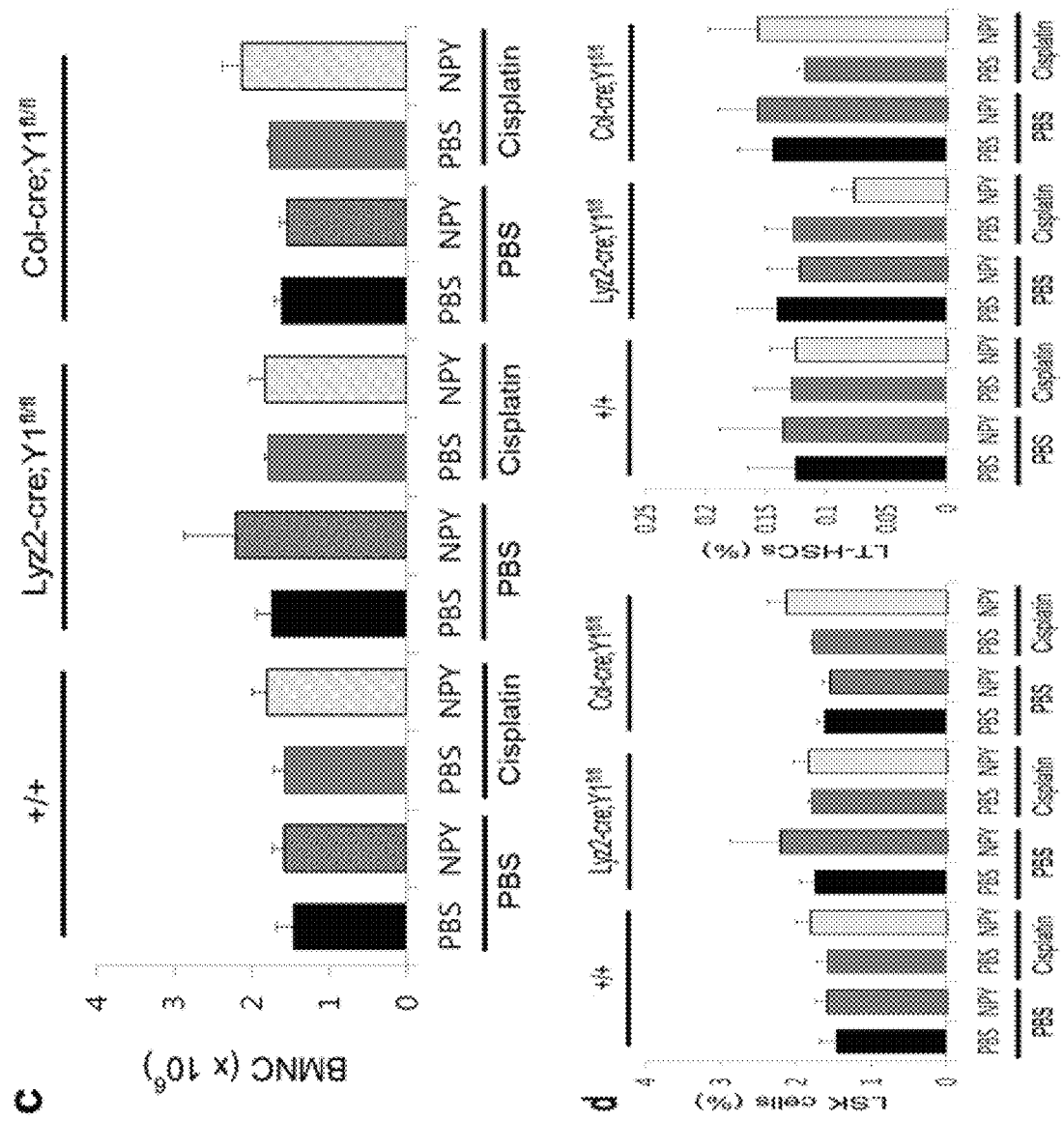
Figure 2:
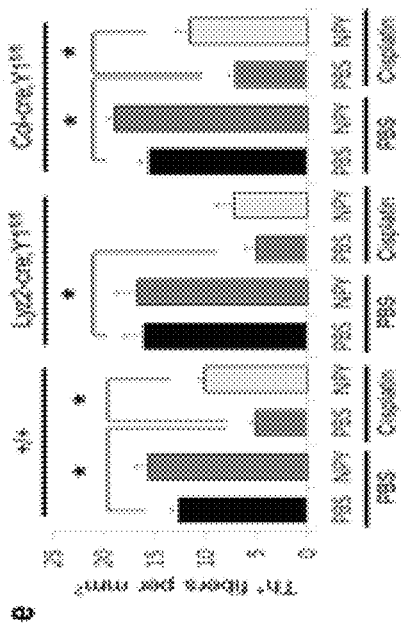
Figure 2:
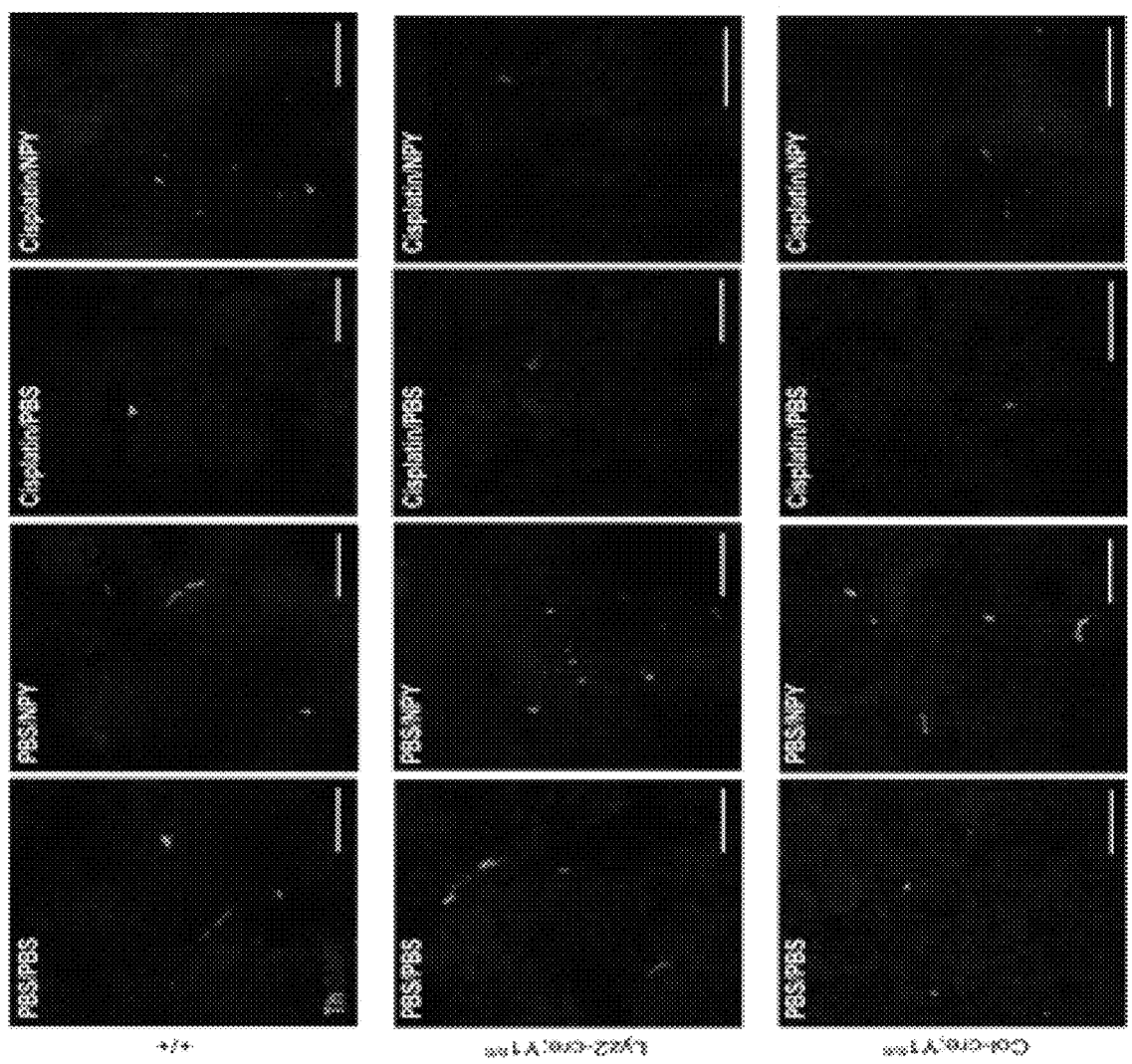
Figure 2:
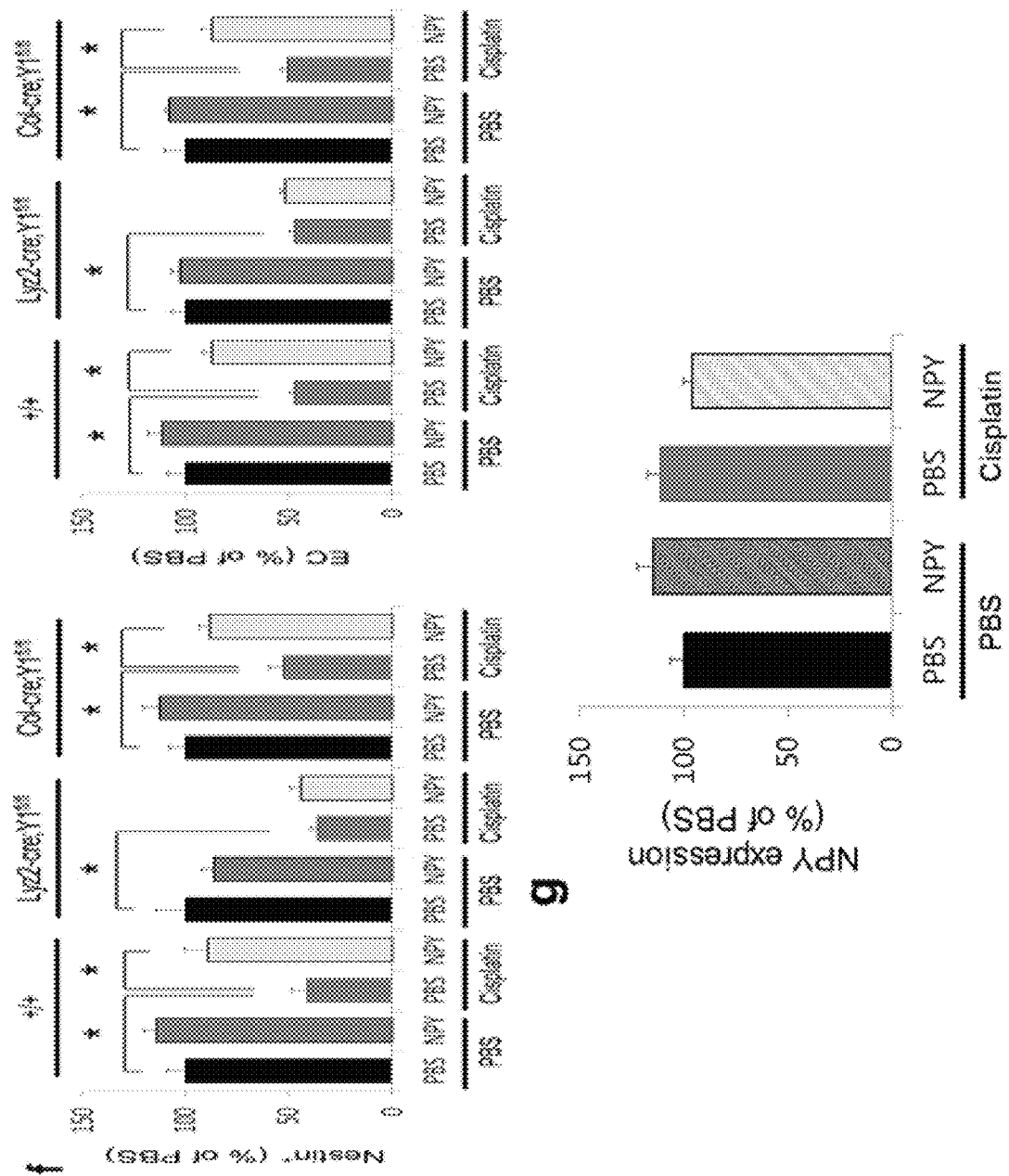
Figure 2:
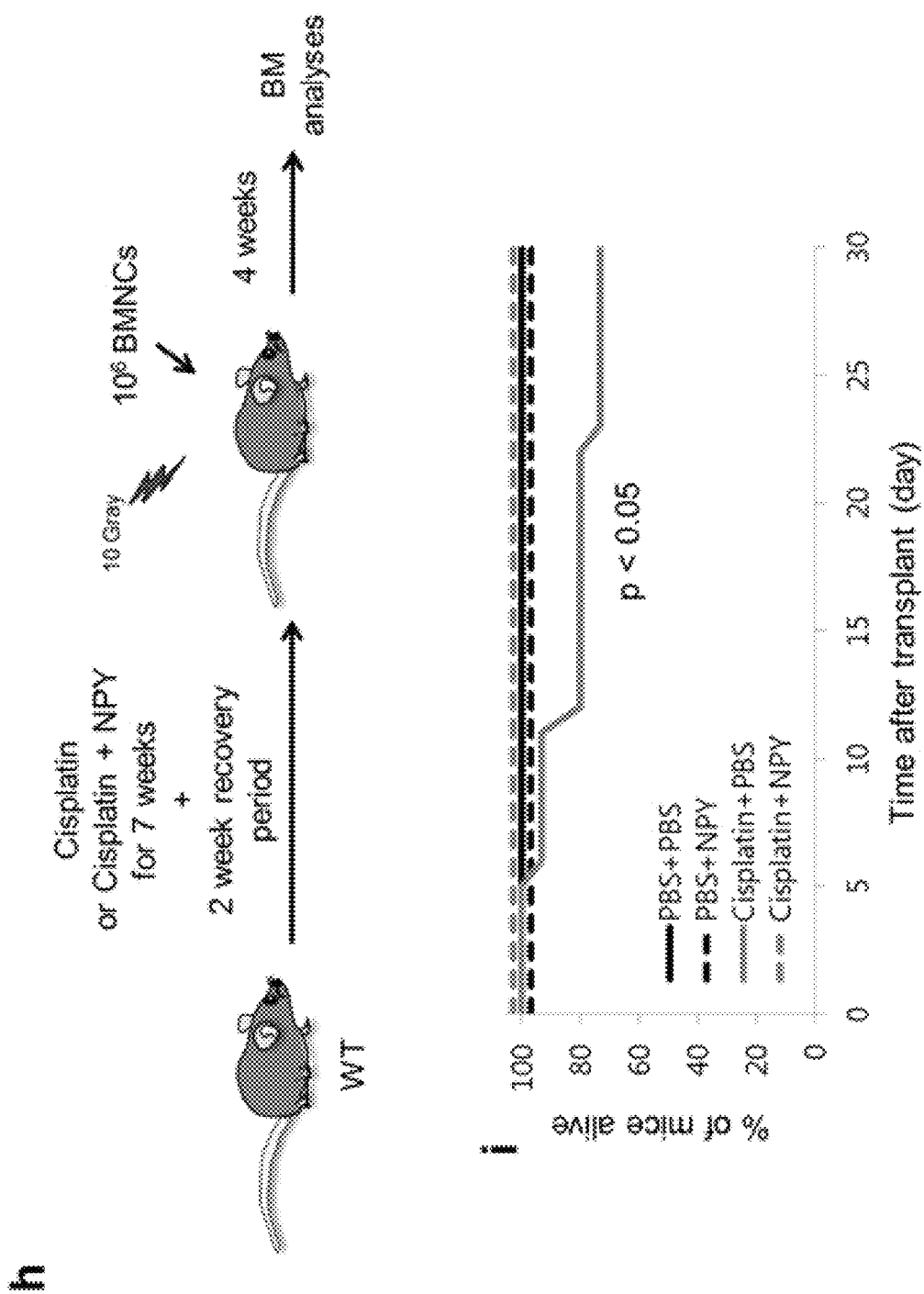
Figure 2:
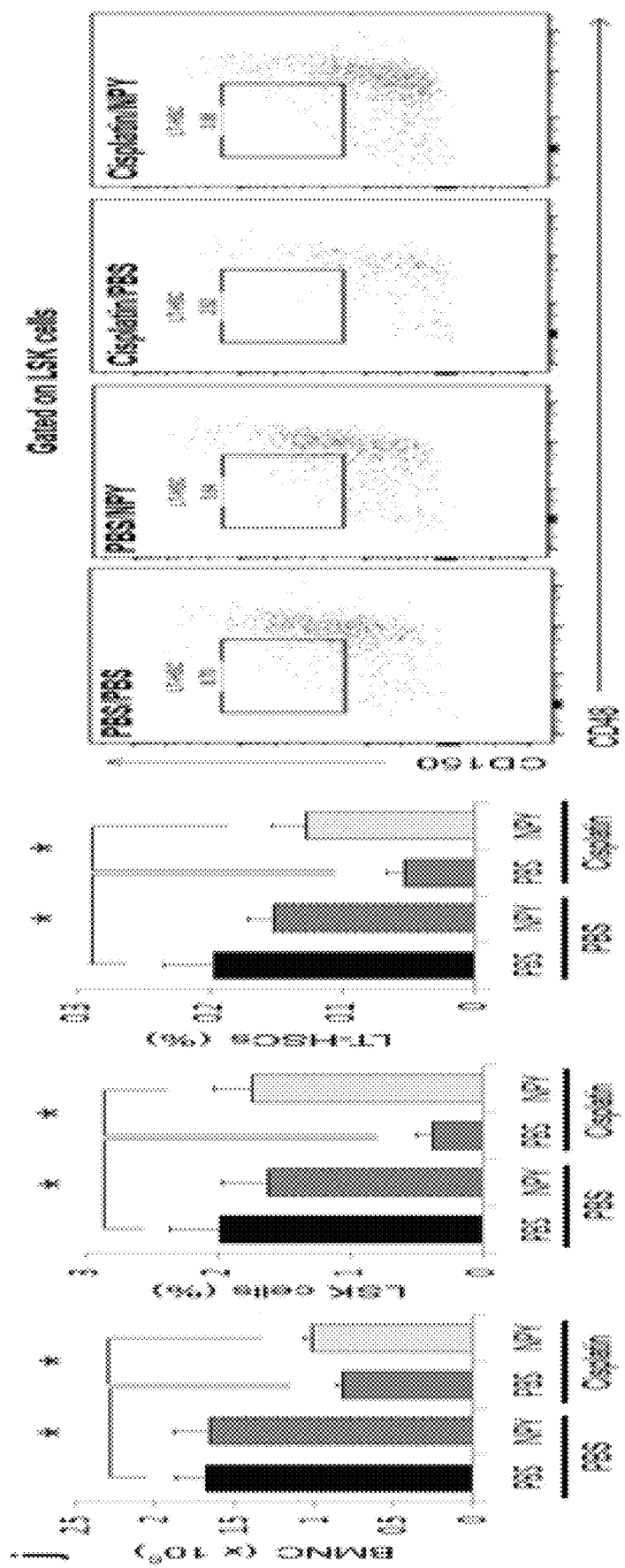
Figure 2:
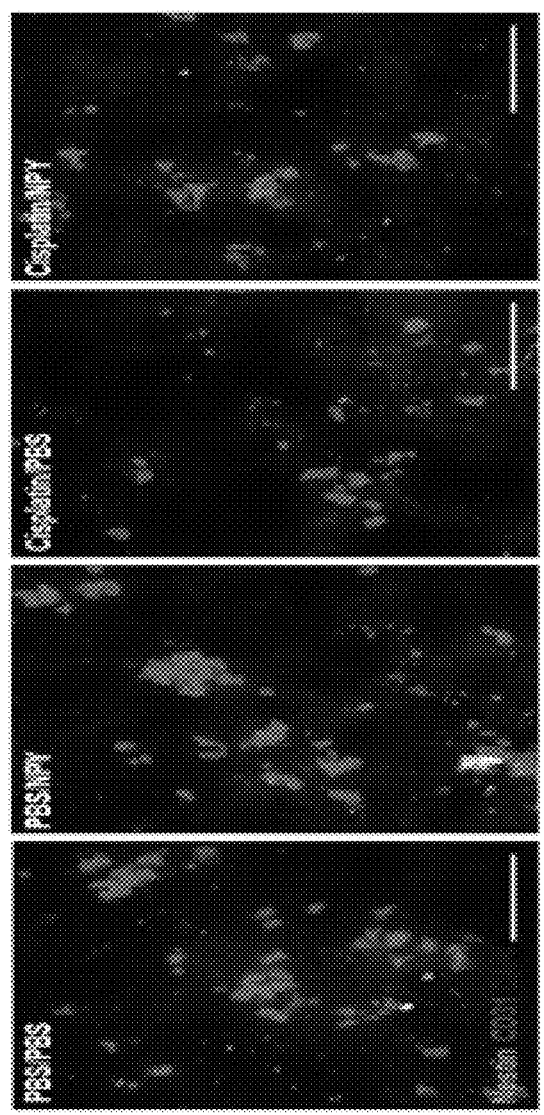
Figure 2:
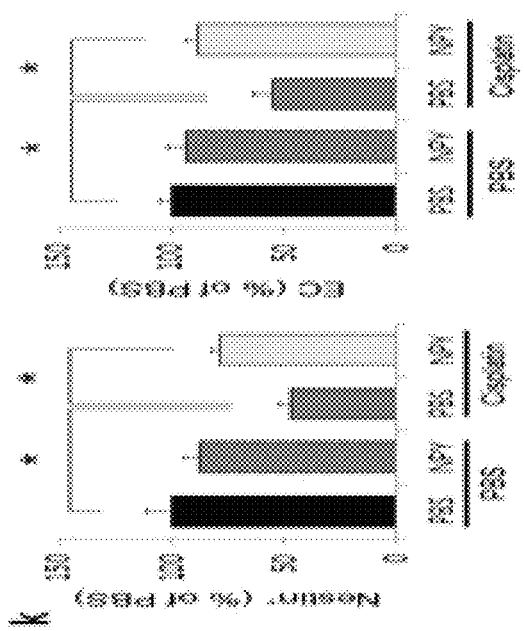

Example 8: Verification of Effect of Mitigating Side Effects of Anticancer Agents Through NPY Administration Next, control, Lyz2-cre; Y1$^{fl/fl}$, or Col1a1-cre; Y1$^{fl/fl}$ mice were treated with seven cycles of cisplatin for the induction of neuropathy. In some animals, NPY was administered during cisplatin chemotherapy. FIG. 2A is an experimental design for determining an effect of the Y1 receptor in the macrophages or osteoblasts in cisplatin-induced neuropathy, after NPY treatment.

The experimental results were illustrated in FIGS. 2B to 2D.

FIG. 2B illustrates a quantitative analysis result of sympathetic neuropathy (after 2 weeks after the last cisplatin injection) in a control group, Lyz2-cre; Y1$^{fl/fl}$ or Col1a1-cre; Y1$^{fl/fl}$ mice treated with cisplatin alone or cisplatin and NPY (n=6-10 mice per group, i.p). Latency illustrates a total time of a nociception signal of mice, that is, until jumping or paw licking.

FIGS. 2C and 2D are diagrams illustrating the number of BMNCs (C), and a percentage of LSK cellas and LT-HSCs (D) in control, Lyz2-cre; Y1$^{fl/fl}$ or Col1a1-cre; Y1$^{fl/fl}$ mice (n=4-6 mice per group) treated in FIG. 2A.

As illustrated in FIGS. 2B to 2D, after 2 weeks after the last injection, the cisplatin-treated mice had sensory neuropathy, whereas BMNCs, LSK cells, and LT-HSCs were normal in all groups.

Further, FIG. 2E is a diagram illustrating a quantitative analysis of a Th$^+$ fiber in BM of each group (n=5-6 mice per group).

FIG. 2F is a diagram illustrating the number (n=5-6 mice per group) of nestin-positive and CD31$^+$ endothelial cells per femoral region of each group.

As illustrated in FIGS. 2B, 2E, and 2F, NPY treatment improved the sensory neuropathy, reduced density of Th$^+$ fibers, and the number of nestin-positive and CD31$^+$ endothelial cells in cisplatin-treated control or Col1a1-cre; Y1$^{fl/fl}$ mice.

Of interest, Lyz2-cre; Y1$^{fl/fl}$ mice did not show NPY-mediated protection of Th$^+$ fibers and perivascular niche cells due to the absence of Y1 receptor in macrophages. These results suggested that NPY induced neuroprotection from cisplatin-induced sympathetic nervous system (SNS) injury through Y1 receptors in macrophages.

To further confirm the effect of neuroprotection by NPY through macrophage Y1 receptor, macrophages were cultured from the BM of control or Lyz2-cre; Y1$^{fl/fl}$ mice and these macrophages were treated with NPY.

Example 8: Verification of Recovery Effect of Bone Marrow Injury Through NPY Administration Next, to evaluate further whether NPY treatment prevents cisplatin-induced mouse death and injury of BM, bone marrow mononuclear cells (BMNCs) were transplanted into cisplatin-treated mice with or without NPY treatment after lethal irradiation. FIG. 2H illustrates an experimental design for verifying whether NPY protects a Th$^+$ fiber from cisplatin-induced bone marrow injury and whether to accelerate posttransplant bone marrow recovery.

The results were illustrated in FIGS. 2I, 2J, and 2K and Table 1 below.

FIG. 2I illustrates a survival result of mice of each group (n=10-15 mice per group).

FIG. 2J is a diagram illustrating the number of BMNCs (left side), a percentage of LSK cells (middle), and LT-HSCs (right side) in BM of WT mice treated with PBS, cisplatin or NPY, which are evaluated after 4 weeks after transplanting bone marrow (n=5-6 mice per group).

FIG. 2K illustrates a percentage of nestin-positive and CD31$^+$ endothelial cells in the femur of each group.

Each data is * p<0.05. An error bar illustrates mean±s.e.m.

TABLE 1

| | PBS/PBS | PBS/NPY | Cisplatin/PBS | Cisplatin/NPY |
|---|---|---|---|---|
| WBC (m/mm$^3$) | 6.1 ± 0.4 | 5.3 ± 0.4 | 2.2 ± 0.4 | 4.4 ± 0.8 * |
| RBC (m/mm$^3$) | 8.7 ± 0.3 | 8.4 ± 0.4 | 6.1 ± 0.8 | 8.0 ± 0.2 * |
| Hgb (g/dl) | 15.1 ± 1.2 | 14.4 ± 0.9 | 12.8 ± 0.8 | 13.3 ± 0.7 |
| HCT (%) | 50.1 ± 8.6 | 49.5 ± 9.3 | 53.5 ± 6.1 | 47.7 ± 4.8 |
| MCV (fl) | 57.5 ± 9.2 | 58.2 ± 8.8 | 66.1 ± 5.2 | 67.6 ± 5.0 |
| MCH (pg) | 17.4 ± 1.5 | 17.35 ± 1.4 | 17.1 ± 0.8 | 19.7 ± 2.3 |
| MCHC (g/dl) | 37.2 ± 8.0 | 33.2 ± 7.6 | 27.0 ± 4.2 | 30.7 ± 4.2 |
| RDW-CV (%) | 20.1 ± 0.5 | 19.4 ± 0.8 | 19.4 ± 0.3 | 20.4 ± 1.2 |
| PLT (m/mm$^3$) | 303 ± 63 | 219.3 ± 65.8 | 165.7 ± 42.4 | 153.7 ± 39.1 |
| MPV (fl) | 13.5 ± 0.9 | 11.4 ± 2.8 | 11.3 ± 2.3 | 11.1 ± 2.1 |

Table 1 is a diagram illustrating an increase in blood cell recovery in NPY-treated mice after cisplatin treatment. A complete blood count was performed by targeting PBS or cisplatin-treated mice after 4 weeks after transplantation and after NPY treatment.

WBC: white blood cell;
RBC: red blood cell;
Hgb: hemoglobin;
HCT: hematocrit;
MCV: mean cell volume;
MCH: mean corpuscular hemoglobin;
MCHC: mean corpuscular hemoglobin concentration;
RDW-CV: red cell volume distribution width-coefficient of variation;
PLT: platelets;
MPV: mean platelet volume As illustrated in FIGS. 2I, 2J, and 2K and Table 1, the NPY treatment enhanced mouse survival and restored the bone marrow function after transplantation. Further, the numbers of nestin-positive and CD31$^+$ endothelial cells in cisplatin-treated mice were restored.

Collectively, the result verified that NPY is required for the maintenance of bone marrow function by protecting SNS fibers and niche cell survival through the Y1 receptor around the blood vessel. A new method for treating chemotherapy-induced bone marrow injury is proposed.

The invention claimed is:

1. A method for inhibiting a side effect of a chemotherapeutic agent in a subject, the method comprising administering to a subject in need thereof an effective amount of a composition consisting of Neuropeptide Y as an active ingredient to inhibit or mitigate the side effect of the chemotherapeutic agent, wherein the side effect is bone marrow injury.

2. The method of claim 1, wherein the chemotherapeutic agent is one or more selected from a group consisting of cisplatin, doxorubicin, etoposide, paclitaxel, doxetaxel, fluoropyrimidine, oxalplatin, belotecan, vinblastine sulfate, cyclophosphamide, actinomycin D, vincristine sulfate, methotrexate, thalidomide, camptothecin, 5-fluorouracil (5-FU), floxuridine, vincristine, gemcitabine, streptozocin, carboplatin, topotecan, irinotecan, vinorelbine, hydroxyurea, valrubicin, meclorethamine, chlorambucil, busulfan, doxifluridine, vinblastin, mitomycin, and mitoxantron.

3. The method of claim 1, wherein the chemotherapeutic agent comprises cisplatin.

4. The method of claim 1, wherein the subject is treated for cancer selected from the group consisting of acute lymphoblastic or lymphocytic leukemia, chronic lymphocytic leukemia, acute non-lymphocytic leukemia, chronic myelogenous leukemia, Hodgkin lymphoma, non-Hodgkin lymphoma, multiple myeloma, brain tumors, breast cancer, colon cancer, stomach cancer, esophagus cancer, gallbladder cancer, liver cancer, pancreatic cancer, head and neck cancer, thyroid cancer, retinoblastoma, neuroblastoma, kidney cancer, bladder cancer, lung cancer, mesothelioma, Ewing's sarcoma, Kaposi's sarcoma, osteosarcomas, ovarian cancer, cervical cancer, uterine cancer, prostate cancer, testicular cancer, penile cancer, and skin cancer.

5. The method of claim 1, wherein the composition is a pharmaceutical composition or a food composition.

* * * * *